US012623202B1

(12) United States Patent　　(10) Patent No.:　US 12,623,202 B1
Parnell　　(45) Date of Patent:　May 12, 2026

(54) COMPOSITIONS AND METHODS FOR ELIMINATING SCENT

(71) Applicant: CAMO DUST INC., Lonoke, AR (US)

(72) Inventor: Michael Parnell, Muncy, PA (US)

(73) Assignee: Camo Dust Inc., Lonoke, AR (US)

( * ) Notice: Subject to any disclaimer, the term of this patent is extended or adjusted under 35 U.S.C. 154(b) by 636 days.

(21) Appl. No.: 18/154,297

(22) Filed: Jan. 13, 2023

Related U.S. Application Data

(60) Provisional application No. 63/267,874, filed on Feb. 11, 2022.

(51) Int. Cl.
　　*B01J 20/16*　　(2006.01)
　　*A61L 9/014*　　(2006.01)
　　*A61L 101/14*　　(2006.01)
　　*A61L 101/24*　　(2006.01)
　　*B01J 20/04*　　(2006.01)
　　*B01J 20/28*　　(2006.01)

(52) U.S. Cl.
　　CPC ............. *B01J 20/165* (2013.01); *A61L 9/014* (2013.01); *B01J 20/048* (2013.01); *B01J 20/28004* (2013.01); *B01J 20/28016* (2013.01); *A61L 2101/14* (2020.08); *A61L 2101/24* (2020.08); *A61L 2209/131* (2013.01); *A61L 2209/22* (2013.01)

(58) Field of Classification Search
　　CPC .. B01J 20/165; B01J 20/048; B01J 20/28004; B01J 20/28016; A61L 9/014; A61L 2101/14; A61L 2101/24; A61L 2209/131; A61L 2209/22
　　See application file for complete search history.

(56) References Cited

U.S. PATENT DOCUMENTS

| | | | | |
|---|---|---|---|---|
| 4,838,922 A | * | 6/1989 | Green | ..................... C05B 17/00 |
| | | | | 71/34 |
| 5,013,335 A | * | 5/1991 | Marcus | .................... B01J 20/18 |
| | | | | 95/902 |
| 5,891,391 A | * | 4/1999 | Fore | .......................... A61L 9/12 |
| | | | | 422/5 |
| 2002/0054919 A1 | * | 5/2002 | Hochwalt | ............... A61L 9/014 |
| | | | | 424/629 |
| 2004/0164029 A1 | * | 8/2004 | Souter | .................... A01N 65/00 |
| | | | | 210/764 |

OTHER PUBLICATIONS

Sheppard, "Zeolites From Sedimentary Rocks", Clays and Clay Minerals. vol. 29. No. 5. pp. 321-322. 1981 (Year: 1981).*

(Continued)

*Primary Examiner* — Daniel C. Mccracken
*Assistant Examiner* — Starfari Teshawn Mcclain
(74) *Attorney, Agent, or Firm* — McKee, Voorhees & Sease, PLC

(57) ABSTRACT

Compositions, systems and methods for using zeolites to eliminate scents and odors are disclosed. The compositions and methods use a zeolite, preferably a dry flowable powder of zeolite, desiccant, and monocalcium phosphate to eliminate scent. Applications of using the compositions and systems are also disclosed, including eliminating human scents and other odors to enhance ability for a hunter, wildlife enthusiast, photographer and the like to access proximity to an animal that is otherwise deterred by scents. Other applications of use are also disclosed.

18 Claims, 4 Drawing Sheets

(56)　　　　　References Cited

OTHER PUBLICATIONS

Sheppard, "Zeolites From Sedimentary Rocks", Clays and Clay Minerals. vol. 29. No. 5. pp. 321-322. 1981 (Year: 1981) Sheppard, "Zeolites From Sedimentary Rocks", Clays and Clay Minerals. vol. 29. No. 5. pp. 321-322. 1981 (Year: 1981) (Year: 1981).*
Mitchell, David, "Gone Huntin'," Fish & Game Finder, Jan. 2000, 1 page.
Structure of Zeolites—Properties and Uses of Zeolites with FAQs, BYJU'S, 2022 [retrieved on Oct. 14, 2022]. Retrieved from the Internet: <URL: https://byjus.com/chemistry/structure-of-zeolites/>, 13 pages.

* cited by examiner

8

10

8

10

12

COMPOSITIONS AND METHODS FOR ELIMINATING SCENT

CROSS REFERENCE TO RELATED APPLICATIONS

This application claims priority under 35 U.S.C. § 119 to provisional patent application U.S. Ser. No. 63/267,874, filed Feb. 11, 2022. The provisional patent application is herein incorporated by reference in its entirety, including without limitation, the specification, claims, and abstract, as well as any figures, tables, appendices, or drawings thereof.

FIELD OF THE INVENTION

The disclosure relates generally to compositions, systems and methods for using the compositions to control scent and namely to eliminate scent. More particularly, the compositions and methods relate to use of a powder zeolite, preferably a dry flowable powder of zeolite, desiccant, and monocalcium phosphate to eliminate scent. The compositions and systems are useful for various applications including eliminating human scents and other odors to enhance ability for a hunter, wildlife enthusiast, photographer and the like to access proximity to an animal that is otherwise deterred by scents. Other applications of use are also disclosed.

BACKGROUND OF THE INVENTION

There are various practical applications in which the control or the elimination of scents and odors is desirable. In particular, when hunting various species of animals, it is desirable to avoid detection by the animal you are hunting. As many species have keen senses of smell, detectable scents on a human, or the scent of a human alone, can deter an animal such as deer, elk, hog, bear, and coyotes. Scents trigger the fear and flight reaction in animals when such human scents are detected. Such keen sense of smell is why many hunters assess the wind direction and speed to avoid detection by the animal being hunted. Various products to mask the scent of humans have been used in the hunting industry. Often such products are liquids and come with various limitations to their use and practical applications. For example, many liquid products mask scent through using agents such as doe urine, doe estrus, fox urine, pine fragrance, acorn fragrance, or other odor masking scents. Some dry powder products have been used which various limitations as well. Thus, there exists a need in the art for dry flowable powder formulations that can be easily and readily dosed and dispensed.

It is therefore an object of this disclosure to provide compositions and systems for dosing and dispensing the compositions to eliminate scents and odors.

It is a further object of the disclosure to provide dry, flowable powder compositions having shelf stability.

It is another object of this disclosure to provide various methods of use for the compositions and systems described herein.

Other objects, embodiments and advantages of this invention will be apparent to one skilled in the art in view of the following disclosure, the drawings, and the appended claims.

SUMMARY OF THE INVENTION

The following objects, features, advantages, aspects, and/or embodiments, are not exhaustive and do not limit the overall disclosure. No single embodiment need provide each and every object, feature, or advantage. Any of the objects, features, advantages, aspects, and/or embodiments disclosed herein can be integrated with one another, either in full or in part.

It is a primary object, feature, and/or advantage of the present invention to improve on or overcome the deficiencies in the art with respect to compositions and methods for eliminating scent and odor.

It is a further object, feature, and/or advantage of the present invention to provide shelf-stable and easy to apply dry powders for hunters to eliminate scents and enhance the hunting experience.

It is a still further object, feature, and/or advantage of the present invention to provide the dry powders with a dosing apparatus to eliminate scents and odors for various applications of use.

According to some aspects of the present disclosure, an odor and scent eliminating composition comprises zeolite, monocalcium phosphate (also referred to as Ammonia Hold), and a desiccant.

According to some additional aspects of the present disclosure, a system for eliminating odor and scent comprises zeolite or the compositions described herein, a dosing apparatus (such as a bag or pouch knitted from wool, cotton, nylon, or the like), and an outer container to provide airtight and waterproof enclosure.

According to additional aspects of the present disclosure, methods of eliminating odor and scent comprise contacting an object or surface with a zeolite or the composition as described herein, and eliminating scents and/or odors. Without being limited to a particular mechanism of action the odor and scent elimination results from the odor and scent being absorbed by the zeolite and monocalcium phosphate framework in the compositions that act like a sponge.

These and/or other objects, features, advantages, aspects, and/or embodiments will become apparent to those skilled in the art after reviewing the following brief and detailed descriptions of the invention. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

BRIEF DESCRIPTION OF THE DRAWINGS

Several embodiments in which the present invention can be practiced are illustrated and described in detail, wherein like reference characters represent like components throughout the several views. The drawings are presented for exemplary purposes and may not be to scale unless otherwise indicated.

Figure 1:
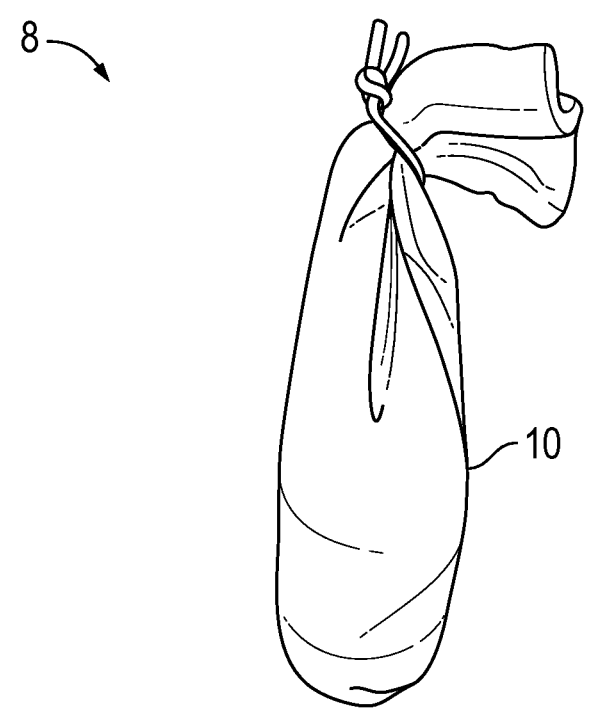
FIG. 1 shows an example of an embodiment of the system wherein the system includes a non-rigid, porous dosing apparatus such that a substance can be dispensed from the dosing apparatus.

An artisan of ordinary skill need not view, within isolated figure(s), the near infinite number of distinct permutations of features described in the following detailed description to facilitate an understanding of the invention.

DETAILED DESCRIPTION OF THE INVENTION

The present disclosure is not to be limited to that described herein, which can vary and are understood by skilled artisans. No features shown or described are essential to permit basic operation of the present invention unless otherwise indicated. It has been surprisingly found that dry flowable powders including zeolite, desiccant and monocalcium phosphate can be effectively dosed in dry form to eliminate scents by absorbing odors and neutralizing the odors.

It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

As used herein, the term "and/or", e.g., "X and/or Y" shall be understood to mean either "X and Y" or "X or Y" and shall be taken to provide explicit support for both meanings or for either meaning, e.g. A and/or B includes the options i) A, ii) B or iii) A and B.

It is to be appreciated that certain features that are, for clarity, described herein in the context of separate embodiments, may also be provided in combination in a single embodiment. Conversely, various features that are, for brevity, described in the context of a single embodiment, may also be provided separately or in any sub-combination.

The methods and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

Unless defined otherwise, all technical and scientific terms used above have the same meaning as commonly understood by one of ordinary skill in the art to which embodiments of the present invention pertain.

The terms "invention" or "present invention" are not intended to refer to any single embodiment of the particular invention but encompass all possible embodiments as described in the specification and the claims.

The term "about," as used herein, refers to variation in the numerical quantity that can occur, for example, through typical measuring techniques and equipment, with respect to any quantifiable variable, including, but not limited to, mass, volume, time, temperature, pH, and log count of bacteria or viruses. Further, given solid and powder handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

The term "configured" describes structure capable of performing a task or adopting a particular configuration. The term "configured" can be used interchangeably with other similar phrases, such as constructed, arranged, adapted, manufactured, and the like. Terms characterizing sequential order, a position, and/or an orientation are not limiting and are only referenced according to the views presented.

As used herein, the term "eliminate", "eliminating" or like terms when used with respect to the disclosure herein, such as eliminating odor refers to a substantial reduction or elimination of scents and odors, such at least about a 90% reduction, 95% reduction, or 100% elimination of the scents and odors as detected by the human olfactory receptors.

As used herein, the term "exemplary" refers to an example, an instance, or an illustration, and does not indicate a most preferred embodiment unless otherwise stated.

As used herein, the term "free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-%, less than 0.01 wt-%, or has 0 wt-%.

As used herein, the term "soft surface" refers to surfaces not classified as hard surfaces. Soft surfaces, include, but are not limited to, textiles, fabrics, woven surfaces, and non-woven surfaces, including those on the clothing or apparel and accessories, such as those of a hunter, wildlife enthu-siast, photographer and the like.

As used herein, the term "scent" refers to a distinctive smell or odor (the terms are herein used interchangeably), including the characteristic smells of a human that is per-ceptible to various species of animals. Such scents are offensive to animals and signal danger.

The "scope" of the present invention is defined by the appended claims, along with the full scope of equivalents to which such claims are entitled. The scope of the invention is further qualified as including any possible modification to any of the aspects and/or embodiments disclosed herein which would result in other embodiments, combinations, subcombinations, or the like that would be obvious to those skilled in the art.

The term "substantially" refers to a great or significant extent. "Substantially" can thus refer to a plurality, majority, and/or a supermajority of said quantifiable variable, given proper context.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

Compositions

According to embodiments, the compositions include zeolite, desiccant, and monocalcium phosphate. The com-positions can include additional functional ingredients and are provided as ready-to-use compositions. Exemplary com-positions are shown in Table 1 in weight percentage. While the components may have a percent actives of 100%, it is noted that Table 1 does not recite the percent actives of the components, but rather, recites the total weight percentage of the raw materials (i.e., active concentration plus inert ingre-dients).

TABLE 1

| Material | First Exemplary Range wt.- % | Second Exemplary Range wt.- % | Third Exemplary Range wt.- % |
|---|---|---|---|
| Zeolite | 60-100 | 80-99 | 90-99 |
| Monocalcium Phosphate | 0-20 | 0.01-20 | 0.01-10 |
| Desiccant | 0-20 | 0.01-20 | 0.01-10 |
| Additional Functional Ingredients | 0-50 | 0-25 | 0-10 |

The compositions are solids, namely powders. The pow-ders are preferably dry flowable powders having an average particle size measured by mesh size (also referred to as U.S. Mesh Size or U.S. Sieve Size), wherein the larger the mesh number the smaller the particle size of the powder. The mesh screen has the defined number of openings in a square inch of screen (e.g., 100 mesh screen has 100 openings in 1 square inch and 325 mesh screen has 325 openings in 1 square inch). Measurement via a mesh size can also be referred to as sieve analysis. Each of these methods rely on two dimensional movement (e.g. horizontal, circular motion and a vertical tapping action) to allow particles to pass through the mesh or sieve. As referred to herein, the average particle size is referenced as one skilled in the art ascertains that in powder forms not all powders are equivalent size (i.e. there is a particle size distribution as the number of particles can have varying sizes), however the average particle size can be measured by the powder that is able to run through a specific sized mesh screen. In embodiments, the compo-sition powders are less than about 100 mesh (149 um or 0.0059 inches). One skilled in the art will ascertain there are other ways to measure particle size distribution, including for example particle fluid dispersion with or without soni-cation to determine the size of particles, grain size, etc.

For the applications of use described herein, it is benefi-cial to provide such a reduced particle size to increase the overall surface area of the zeolite to maximize the capacity of the compositions to neutralize and thereby eliminate scent. The compositions also have a low free moisture (FM) content, in some embodiments less than about 12%, less than about 11%, less than about 10%, less than about 9%, or less than about 8%. In preferred embodiments, the FM content is less than about 8%. Without being limited to a particular mechanism of action, the combined decrease in average particle size to less than about less than about 100 screen mesh (149 um or 0.0059 inches) and a decrease in FM content is less than about 10% or preferably less than about 8%, results in a more efficacious and a more flowable powder.

Zeolite

The composition comprises a zeolite. Zeolites are porous minerals with high absorbency and ion-exchange capacity, stated another way they act like sponges to neutralize and eliminate scents and odors. Zeolites are crystalline solids that contain micropores in their structures that is made up of three primary components, oxygen, silicon, and aluminum. The molecular structure of zeolite can include a dense network of $AlO_4$ and $SiO_4$ that create cavities where water and other polar molecules or ions are inserted/exchanged. The chemical makeup of zeolites include hydrated calcium aluminosilicate. In embodiments the compositions comprise a natural zeolite (CAS 1318-2-1). Zeolites can also be referred to as clinoptilolite (CAS 12173-10-3). The source of zeolites can be a variety of sedimentary origins. The zeolites act as sponge-like material to neutralize and thereby elimi-nate odors and scent.

The zeolite is screened to a desired size for use in a variety of dosing apparatus. The size of the zeolite will be selected based on the dosing apparatus for a particular application of use. Zeolites are commercially available in various granular, powdered, or micronized forms. Zeolites are also commer-cially available in purified forms, all available as powders. In embodiments, the zeolite has an average particle size that is less than about less than about 100 screen mesh (149 um or 0.0059 inches).

In some embodiments, the zeolite is included in the composition at an amount of at least about 60 wt-% to about 100 wt-%, about 65 wt-% to about 100 wt-%, about 70 wt-% to about 100 wt-%, about 75 wt-% to about 100 wt-%, about 80 wt-% to about 100 wt-%, about 85 wt-% to about 100 wt-%, about 90 wt-% to about 100 wt-%, or about 95 wt-% to about 100 wt-%. In further embodiments, the zeolite is included in the composition at an amount of at least about 60 wt-% to about 99 wt-%, about 65 wt-% to about 99 wt-%, about 70 wt-% to about 99 wt-%, about 75 wt-% to about 99 wt-%, about 80 wt-% to about 99 wt-%, about 85 wt-% to about 99 wt-%, about 90 wt-% to about 99 wt-%, or about 95 wt-% to about 99 wt-%. In addition, without being limited according to the invention, all ranges recited are inclusive of the numbers defining the range and include each integer within the defined range.

Monocalcium Phosphate

The composition can comprise monocalcium phosphate, IUPAC name calcium bis(dihydrogen phosphate), $Ca(H_2PO_4)_2$. The monocalcium phosphate can be purchased commercially or made by processes such as combining phosphoric acid, water, and brown mud, such as disclosed in U.S. Pat. No. 4,838,922, which is incorporated herein by reference in its entirety. Monocalcium phosphate can also be made by reacting a calcium source (e.g. calcium hydroxide also referred to as limewater) with phosphoric acid. Without being limited to a particular mechanism of action, the monocalcium phosphate act as an "ammonia hold" or an "ammonia suppressant" in the compositions. Beneficially, in combination with the zeolites the components neutralize and eliminate odors and scents.

In some embodiments, the monocalcium phosphate is included in the composition at an amount of at least about 0 wt-% to about 20 wt-%, about 0.01 wt-% to about 20 wt-%, about 0.01 wt-% to about 15 wt-%, about 0.01 wt-% to about 10 wt-%, about 0.01 wt-% to about 9 wt-%, about 0.01 wt-% to about 8 wt-%, about 0.01 wt-% to about 7 wt-%, about 0.01 wt-% to about 6 wt-%, about 0.01 wt-% to about 5 wt-%, about 0.01 wt-% to about 4 wt-%, about 0.01 wt-% to about 3 wt-%, about 0.01 wt-% to about 2 wt-%, or about 0.01 wt-% to about 1 wt-%. In addition, without being limited according to the invention, all ranges recited are inclusive of the numbers defining the range and include each integer within the defined range.

Desiccant

The composition can comprise a desiccant, such as an activated alumina desiccant. Activated alumina desiccants can include non-fibrous activated aluminum oxide (various alumina desiccants are commercially available). Activated alumina can be manufactured from aluminum hydroxide by dehydroxylating it in a way that produces a highly porous material. As described herein activated alumina desiccants can include aluminosilicates.

The activated alumina desiccant beneficially reduces the free moisture content of the composition and enhances the free-flowing powder of the compositions. The activated alumina is a desiccant as it prevents the zeolite in the composition from getting wet and absorbing water by instead absorbing water from the air. The activated alumina desiccant beneficially functions to decrease the hygroscopicity of the composition while working as a desiccant through adsorption of the water in the air. Without being limited to a particular mechanism of action, as air passes through the dispensing apparatus containing the activated alumina desiccant, the moisture (i.e., water) sticks to the activated alumina desiccant and is trapped, thereby enabling the air that passes through the activated dispensing apparatus or the composition to dry out.

In some embodiments, the desiccant is included in the composition at an amount of at least about 0 wt-% to about 20 wt-%, about 0.01 wt-% to about 20 wt-%, about 0.01 wt-% to about 15 wt-%, about 0.01 wt-% to about 10 wt-%, about 0.01 wt-% to about 9 wt-%, about 0.01 wt-% to about 8 wt-%, about 0.01 wt-% to about 7 wt-%, about 0.01 wt-% to about 6 wt-%, about 0.01 wt-% to about 5 wt-%, about 0.01 wt-% to about 4 wt-%, about 0.01 wt-% to about 3 wt-%, about 0.01 wt-% to about 2 wt-%, or about 0.01 wt-% to about 1 wt-%. In addition, without being limited according to the invention, all ranges recited are inclusive of the numbers defining the range and include each integer within the defined range.

Additional Functional Ingredients

The components of the composition can further be combined with various functional components suitable for uses disclosed herein. In some embodiments, the compositions including the zeolite, desiccant, and monocalcium phosphate make up a large amount, or even substantially all of the total weight of the compositions. For example, in some embodiments few or no additional functional ingredients are disposed therein. In other embodiments, the compositions do not add and are free of liquid components, odor masking components and/or fragrances. As the compositions eliminate scents there are no additional functional ingredients added that would impart a scent or interfere with the dry powder form of the compositions.

In other embodiments, additional functional ingredients may be included in the compositions. The functional ingredients provide desired properties and functionalities to the compositions. For the purpose of this application, the term "functional ingredient" includes a material that when dispersed in the composition provides a beneficial property in a particular use. Some particular examples of functional materials can include for example, dispersants, stabilizing agents, aesthetic enhancing agents that do not impact scents, buffers, and the like.

According to embodiments of the invention, the various additional functional ingredients may be provided in a composition in the amount from about 0 wt-% and about 50 wt-%, from about 0 wt-% and about 40 wt-%, from about 0 wt-% and about 30 wt-%, from about 0 wt-% and about 25 wt-%, from about 0.01 wt-% and about 25 wt-%, from about 0.1 wt-% and about 25 wt-%, or from about 0.1 wt-% and about 10 wt-%. In addition, without being limited according to the invention, all ranges recited are inclusive of the numbers defining the range and include each integer within the defined range.

System(s)

The system(s) for eliminating scent include the compositions described herein and a dosing apparatus and components thereof. In addition, the system(s) for eliminating scent can include the zeolite alone (instead of the composition) and the dosing apparatus. The system(s) can further include a container or housing for the dosing apparatus containing the compositions (or the zeolite). As described herein, in various embodiments the dosing apparatus contains the composition (or the zeolite), however one skilled in the art will ascertain from the description herein that each component of the system(s) could be provided separately and assembled at various points of use.

Beneficially the size of the dosing apparatus and container or housing can be decreased as a result of the powder zeolite or the composition having an average particle size measured by mesh size less than about 100 screen mesh (149 um or 0.0059 inches). The decrease in particle size increases the overall surface area for eliminating scents and odors while decreasing the size of the powder and thereby decreasing the size of the dosing apparatus and container or housing.

Figure 2:
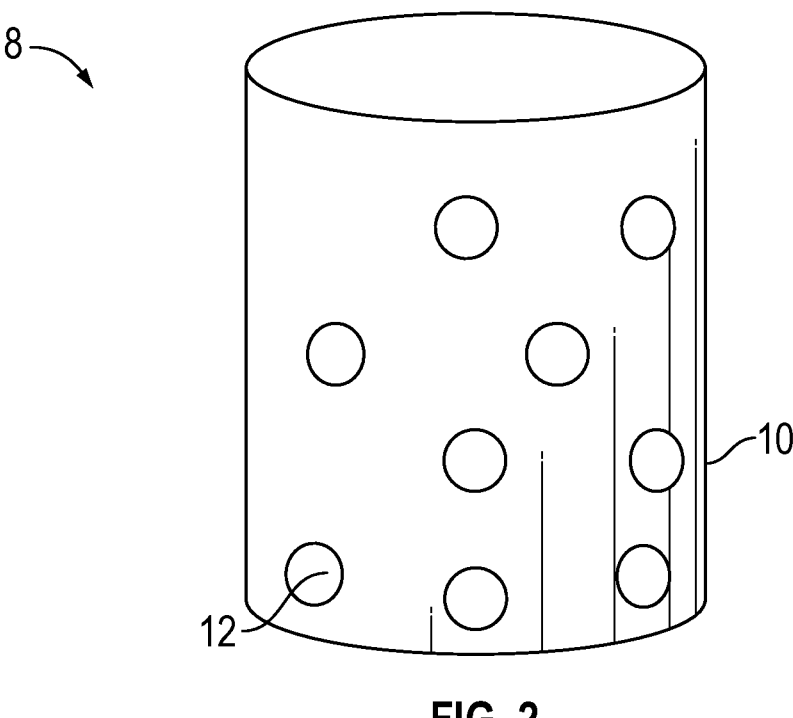
FIG. 2 shows an example of an embodiment of the system wherein the system includes a rigid, porous dosing apparatus such that a substance can be dispensed from the dosing apparatus.

Various types of dosing apparatus can be used for the system(s) for eliminating scents. FIG. 1 shows an exemplary system 8 that includes an exemplary dosing apparatus 10, wherein the dosing apparatus 10 is a porous (i.e., breathable) housing constructed of a fabric material such that the dosing apparatus 10 is non-rigid. While the dosing apparatus 10 of FIG. 1 is provided as an example of one embodiment, other exemplary porous housings/dosing apparatuses 10 can take any number of shapes and sizes that allow for the compositions (or the zeolite) to be dispensed from the porous housing/dosing apparatus 10 (e.g., upon shaking or other agitation to dispense a desired quantity or amount thereof). As shown in FIG. 1, in at least one embodiment, a porous housing/dosing apparatus 10 can look like a bag or pouch (such as a sock), or other fabric (inclusive of all porous textiles) container that is selected based on the particle size of the composition (or the zeolite) to have a controlled dispensing thereof. The porous housing/dosing apparatus 10 can be made of various porous materials, such as knitted from wool, cotton, nylon, or the like. While the exemplary porous housing/dosing apparatus 10 of FIG. 1 may not appear porous in the figure, the fabric and/or fabric-like material of which the porous housing/dosing apparatus 10 is made of is porous such that the composition (or the zeolite) can be dispensed from the porous housing/dosing apparatus 10. Additionally, in other embodiments, the dosing apparatus 10 is a porous housing constructed of a hard and/or rigid material such that the dosing apparatus 10 maintains its shape. FIG. 2 shows an example of an embodiment of the system 8 in which the porous housing/dosing apparatus 10 is constructed of a hard and/or rigid material such that the porous housing/dosing apparatus 10 keeps its shape. As shown in FIG. 2, in embodiments which include a rigid porous housing/dosing apparatus 10, the porous housing/dosing apparatus 10 can include perforations, openings, holes, and/or apertures 12 which render the dosing apparatus 10 to be porous. Such perforations, openings, holes, and/or apertures 12 can number from 1 to n where n is any number greater than 1, can be included on any suitable portion of the porous housing/dosing apparatus 10, can be of any suitable size and/or shape, and can be arranged in any suitable formation. In some embodiments, such perforations, openings, holes, and/or apertures 12 can be sized large enough so that the compositions (or the zeolite) can be dispensed from the porous housing/dosing apparatus 10 (e.g., upon shaking or other agitation to dispense a desired quantity or amount thereof). The perforations, openings, holes, and/or apertures 12 appearing in FIG. 2 may not be drawn to size but rather are provided for easier visualization. In embodiments which include a rigid porous housing/dosing apparatus 10, the porous housing/doping apparatus 10 can be made from various materials, such as metal, plastic, wood, and the like.

Figure 3:
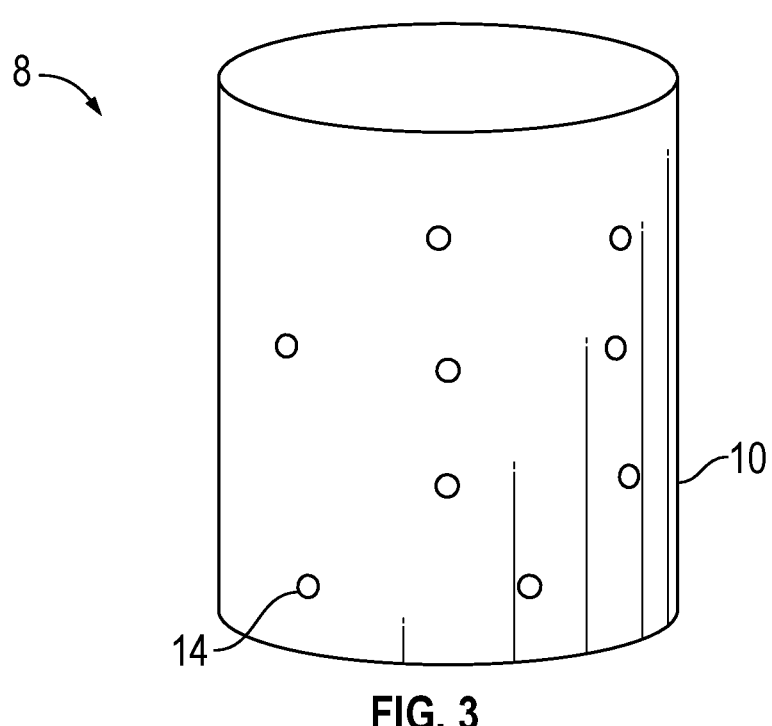
FIG. 3 shows an example of an embodiment of the system wherein the system includes a rigid, porous dosing apparatus wherein scents and/or air can pass through the dosing apparatus.
Figure 4:
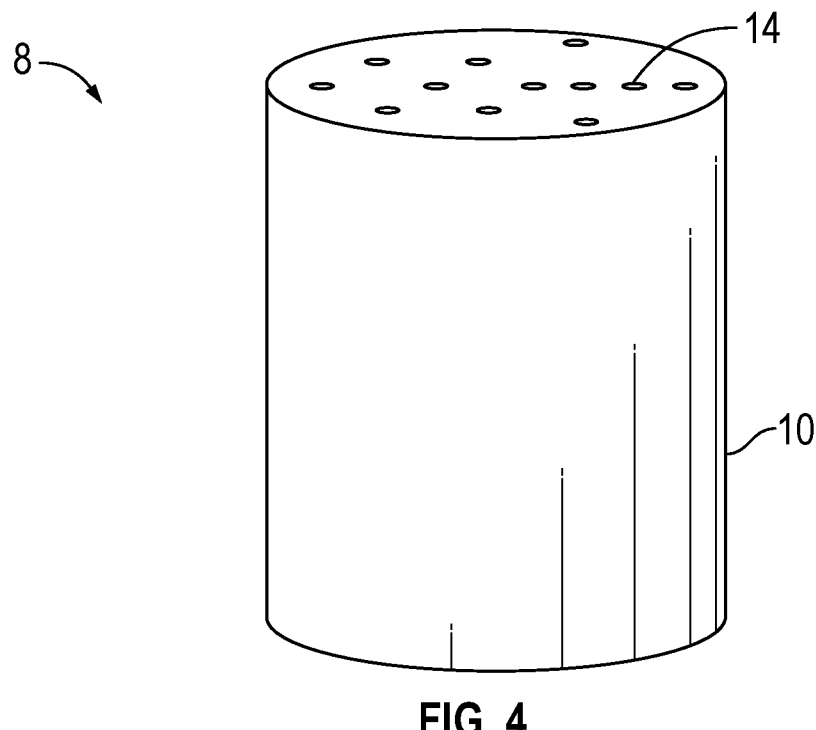
FIG. 4 shows an example of an embodiment of the system wherein the system includes a rigid, porous dosing apparatus wherein scents and/or air can pass through the dosing apparatus.

In further alternative exemplary embodiments of the system 8, porous housings/dosing apparatuses 10 can be used that do not dispense the composition (or the zeolite) and instead contain the composition (or the zeolite) therein and instead allow for scents and/or air to pass through the porous housing/dosing apparatus 10 and be neutralized. Such embodiments, one skilled in the art will ascertain, can have one or more apertures 14 with a porous size that is smaller than the size of the composition (or the zeolite) contained therein. Such embodiments, wherein scents and/or air passes through the porous housing/doping apparatus 10, via the one or more apertures 14, rather than the composition (or zeolite) being dispensed, can resemble such dosing apparatuses/porous housings 10 wherein the composition (or zeolite) is dispensed except that the embodiments in which air and/or scents pass through the dosing apparatus/porous housing 10 can have one or more apertures 14 with a porous size that is smaller than the size of the composition (or zeolite). FIG. 3 shows an exemplary system 8 that includes a porous housing/dosing apparatus 10 with one or more apertures 14 arranged on one or more sides of the porous housing/dosing apparatus 10. FIG. 4 shows an exemplary system 8 that includes a porous housing/dosing apparatus 10 with one or more apertures 14 arranged on the top of the porous housing/dosing apparatus 10. The apertures 14 appearing in FIGS. 3 and 4 may not be drawn to size but rather are provided for easier visualization. The exemplary apertures 14 appearing in FIGS. 3 and 4 can be sized smaller than the size of the composition (or the zeolite) contained within the porous housing/dosing apparatus 10. In embodiments wherein scents and/or air passes through the porous housing/dosing apparatus 10, the one or more apertures 14 can number from 1 to n where n is any number greater than 1, can be included on any suitable portion of the porous housing/dosing apparatus 10, can be of any suitable size and/or shape, and can be arranged in any suitable formation. It should be noted that the lead lines for reference numeral 14 in each of FIGS. 3 and 4 point to only one aperture, however, each of the one or more apertures shown in FIGS. 3 and 4 constitute apertures 14. In embodiments of the system 8 that include a porous housing/dosing apparatus 10 wherein scents and/or air pass through the porous housing/dosing apparatus 10 rather than dispensing the composition (or the zeolite), the porous housing/dosing apparatus 10 can resemble that of FIG. 1 in that the porous housing/dosing apparatus 10 is made of a fabric material and can look like a bag or pouch except that the pores of the porous housing/dosing apparatus are sized smaller than the size of the composition (or the zeolite).

Figure 5:
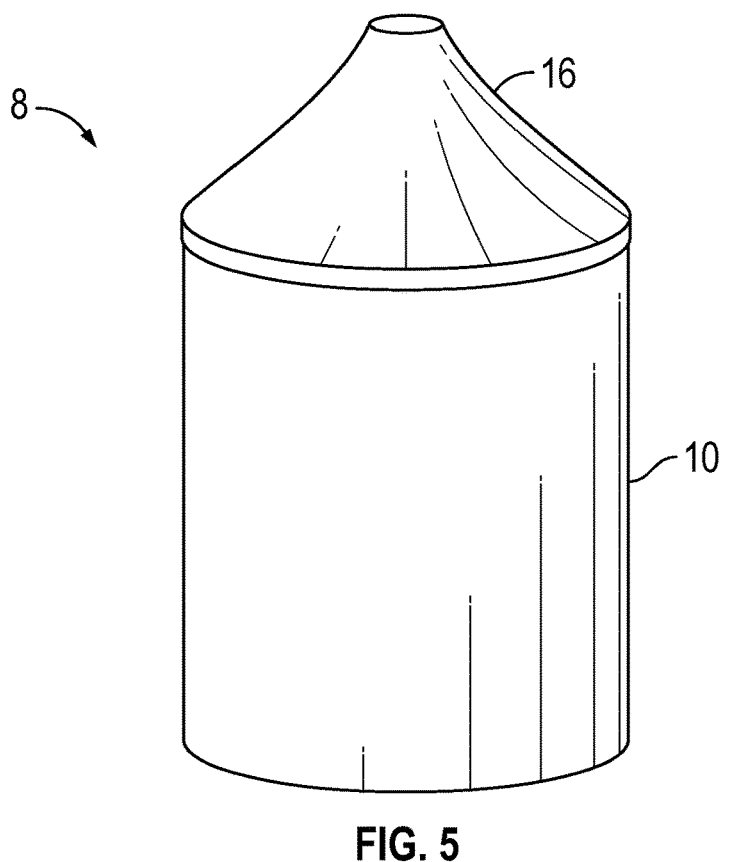
FIG. 5 shows an example of an embodiment of the system wherein the system includes a dosing apparatus comprising a dispensing element.
Figure 6:
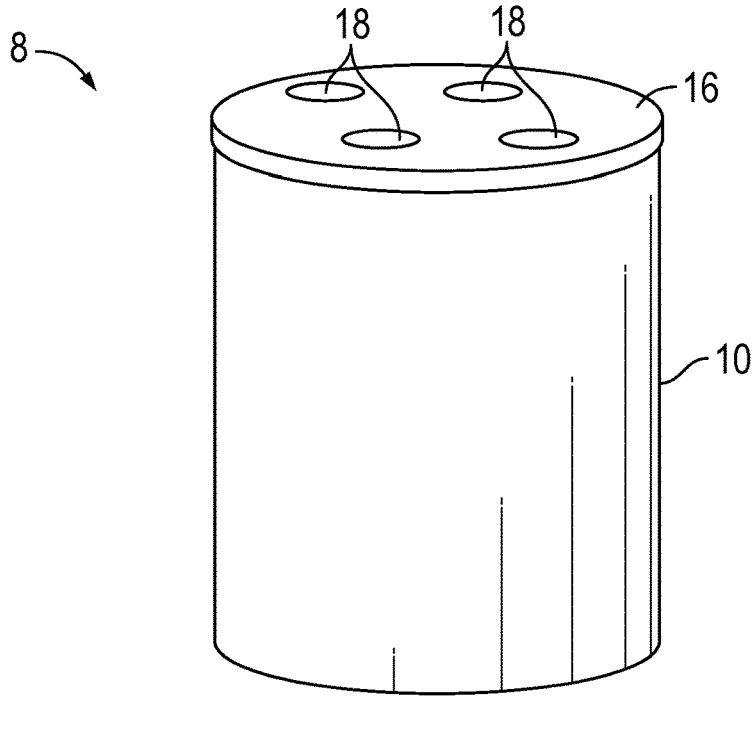
FIG. 6 shows an example of an embodiment of the system wherein the system includes a dosing apparatus comprising a dispensing element.

In still further exemplary embodiments of the system 8, the dosing apparatus 10 can be a non-porous housing. Instead, the dosing apparatus 10 can have a dispensing element 16, such as a lid (e.g. perforated lid or sealed lid), squeeze top, or the like. The dispensing element 16 is configured to dose, administer, or otherwise apply the composition (or the zeolite) onto a surface or object. For example, the dosing apparatus 10 can be a squeezable container that expels the composition (or the zeolite) into the air or onto a surface in need of treatment for elimination of scent. Exemplary non-porous housings can take any number of shapes and sizes that allow for the compositions (or the zeolite) to be housed until a point of dispensing (e.g., upon squeezing, shaking the content out of the dispensing element, or the like) such that a desired quantity or amount thereof is dispensed. FIG. 5 shows an exemplary embodiment of the system 8 that includes a dosing apparatus 10, wherein the dosing apparatus 10 is non-porous and squeezable. The embodiment of FIG. 5 includes a dispensing element 16, wherein the dispensing element 16 is a squeeze top. In the embodiment of FIG. 5, when the dosing apparatus 10 is squeezed by a user/operator, the composition (or the zeolite) contained within the dosing apparatus 10 can be dispensed from the dosing apparatus 10 via the dispensing element 16. FIG. 6 shows another exemplary embodiment of the system 8 that includes a dosing apparatus 10 wherein the dosing apparatus 10 is non-porous. The embodiment of FIG. 6 includes a dispensing element 16, wherein the dispensing element 16 is a perforated lid that includes perforations 18. Such perforations 18 can be of any suitable shape, size, and/or arrangement such that the composition (or the zeolite) can be dispensed via the perforations 18. In the embodiment of FIG. 6, when a user/operator shakes, upends, or otherwise agitates the dosing apparatus 10, the composition (or the zeolite) contained in the dosing apparatus 10 can be dispensed from the dosing apparatus 10 via the perforations 18 of the dispensing element 16.

In embodiments, the dosing apparatus provides a determined or measured amount of the composition (or the zeolite) for one or more applications of use thereof. In various embodiments, it is desired for the dosing apparatus to contain sufficient quantity of the composition (or the zeolite) for multiple applications of use. As described in the Methods of Use the amount of the composition (or the zeolite) applied for an application of use can vary depending upon factors including the surface area to be treated, wind and other weather conditions, and/or the particular application for the use (e.g., type of game that is being hunted).

In some embodiments, the dosing apparatus can contain from about 1 oz. to about 120 oz., from about 2 oz. to about 60 oz, from about 3 oz. to about 30 oz., or from about 4 oz. to about 12 oz. of the zeolite or the composition. In embodiments where a user will be transporting the system(s) for use 'on the go' (e.g. a hunter), the dosing apparatus preferably contains from about 1 oz. to about 20 oz., from about 1 oz. to about 12 oz, from about 1 oz. to about 10 oz., or from about 2 oz. to about 10 oz. of the zeolite or the composition. In addition, without being limited according to the invention, all ranges recited are inclusive of the numbers defining the range and include each integer within the defined range. Such volumes of the dosing apparatus can provide an estimated 4-12 uses, 6-10 uses, or on average about 6-8 uses. However, as one skilled in the art will ascertain from the disclosure herein, varying amounts of the zeolite or the composition are used for different applications of use and the average rate of consumption of the zeolite, or the composition will vary and is not intended to limit the scope of the invention as described herein.

Figure 7A:
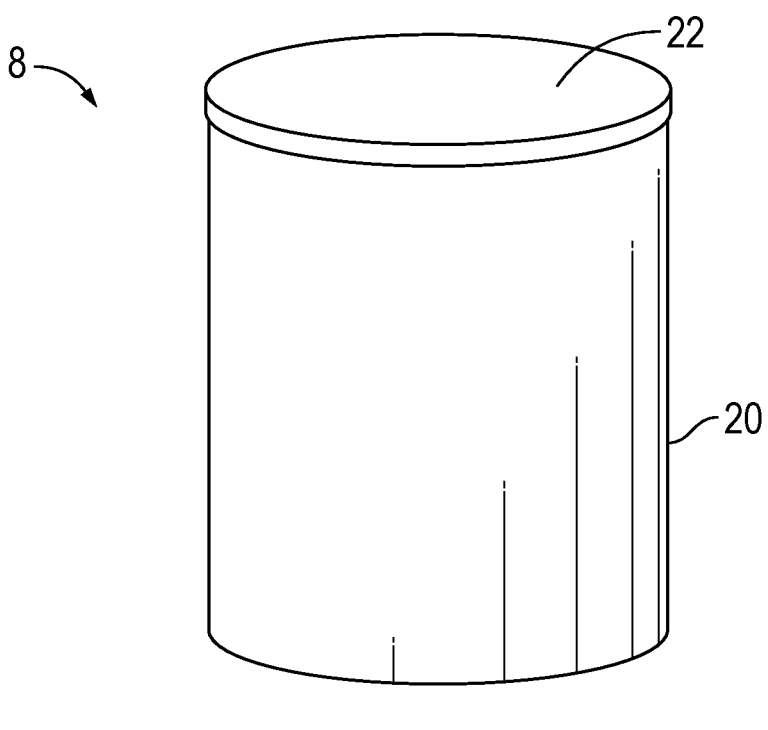
FIG. 7A shows an example of an embodiment of the system wherein the system includes an outer container and a removable lid positioned on the outer container.
Figure 7B:
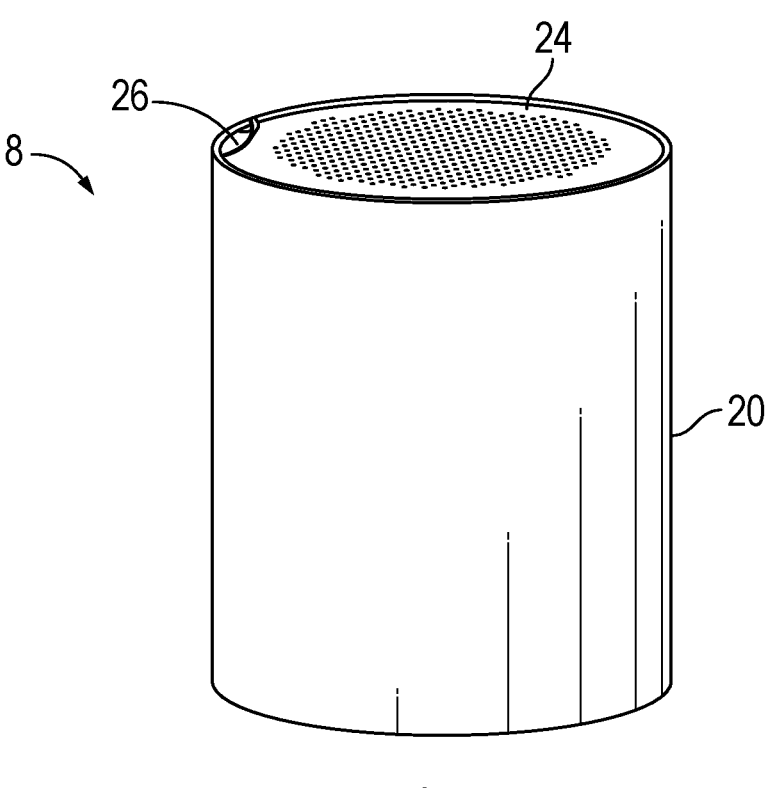
FIG. 7B shows an example of the same embodiment of the system of FIG. 7A wherein the removable lid is removed from the outer container.

Some embodiments of the system 8 can further include an outer container 20 to house the zeolite or composition, dosing apparatus 10 and/or dispensing element 16. The outer container 20 can act as a housing for the dosing apparatus 10 and is beneficially sealed to provide shelf-stability. The outer container 20 is sealed to further limit any exposure of its contents to water and moisture to prolong the shelf-stability and efficacy thereof. In embodiments, the outer container 20 provides a shelf-stable zeolite or composition for at least about 2 years, or at least about 1 year after the removal of the seal from the container. Beneficially the sealed outer container 20 has an indefinite shelf-stability as its contents are protected from any contact with moisture as the outer container 20 is both airtight and waterproof. The outer container 20 can take various shapes and sizes to fit the dosing apparatus 10 and the amount of the zeolite or composition contained therein. In an exemplary embodiment the outer container 20 is a sealed can or jar with a lid 22 to be replaced upon removal of the seal 24. FIGS. 7A and 7B show an exemplary embodiment of the system 8 that includes an outer container 20. FIG. 7A shows the exemplary outer container 20 wherein the removable lid 22 is positioned on the outer container 20. FIG. 7B shows the exemplary outer container 20 wherein the removable lid 22 is removed from the outer container 20 such that the seal 24 of the outer container 20 is visible. The seal 24 can be positioned between the outer container 20 and the removable lid 22 and can render the outer container 20 both airtight and waterproof. The removable lid 22 can be removed from and/or positioned on the outer container 20 when the seal 24 is positioned on the outer container 20 and when the seal 24 is removed from the outer container 20. As shown in the embodiment of FIGS. 7A and 7B, some embodiments include a pull tab 26 on the seal 24 to assist in removing the seal 24 from the outer container 20.

Methods of Use

The compositions and systems employing the compositions beneficially do not mask or simply cover scents. The compositions are efficacious in eliminating scents or stated another way in neutralizing scents. As referred to herein the elimination of scents is referring to all detectable scents. Without being limited to a particular mechanism of action for applications of use described herein, the combined decrease in average particle size to less than about less than about 100 screen mesh (149 um or 0.0059 inches) and a decrease in FM content is less than about 10% or preferably less than about 8%, results in an increased surface area of the particles to neutralize and thereby eliminate odors as seen by increased absorption of odors, as well as a more flowable powder.

There are various applications of use for eliminating scents. In an exemplary embodiment, the compositions or systems are used by hunters to eliminate scents that would otherwise warn off or alert the game they are hunting to their presence as a result their ability to use their sense of smell to alert themselves to danger. In such an embodiment, the composition is applied to various surfaces on or around the hunter to eliminate scents. Various other applications of use can employ the compositions or systems, such as wildlife enthusiasts, photographers, or the like who do not want to be detected by animals they are searching for and want to have a close proximity to.

Beneficially, in any of these applications of use where the compositions are applied outdoors there are benefits to the compositions being a dry powder. In particular, this overcomes a problem in the art where the spraying liquids onto materials or surfaces when temperatures can be below freezing interferes with the ability of the liquids to control scents. Instead, the powder compositions are applied to soft surfaces, such as the clothing, bags, or accessories of the hunter, wildlife enthusiast, photographer, or the like to eliminate scents that would warn off the game or wildlife.

Another application of using the zeolite, compositions, and/or the systems described herein, is to provide a way to check or detect wind, including wind direction. In an embodiment, the zeolite, compositions, and/or the systems can be used to see the direction of wind when an amount of the zeolite or composition is dispensed into the air. The powder provides a visible indicator of the direction and general speed of the wind. This provides a hunter, wildlife enthusiast, photographer, or the like valuable information to see the direction of wind in relation to an animal. The dosing of the zeolite or composition into the air further eliminates odors then moving into the direction of the animal.

As one skilled in the art can ascertain from the disclosure herein, there are various other non-hunting and even indoor applications of use for the compositions and the systems for eliminating odors. In an embodiment, the compositions or the systems can be used in a porous dosing apparatus that contains the composition (or the zeolite) that can be added to a location in need of scent, namely odor, neutralization and elimination. For example, the porous dosing apparatus can be in the form of a sachet, pocket, ball, or other dosing apparatus, that is suitable to be placed into a clothes bag, laundry bag, purse, hunting sack, drawer, shoe, car, bathroom or any room with an undesirable odor, in or near cat litter, etc.

The zeolite and compositions can be applied to objections and surfaces, such as soft surfaces, into the wind, etc. using a variety of methods. For example, these will vary depending upon the dosing apparatus of the system. The zeolite or compositions can contact the object or surface using any of numerous methods for applying a powder, such as spraying the powder, shaking the zeolite or composition out of the dosing apparatus, or the like. Without being limited to the contacting according to the invention, the powder can be applied to or brought into contact with an object or surface by any conventional methods.

The zeolite or compositions are in contact with a surface or object for a sufficient amount of time to neutralize and thereby eliminate the scent or odor. In an aspect, the surface or object is contacted with the zeolite or compositions for at least a few seconds to a few minutes. Beneficially, the scent begins to neutralize and become eliminated immediately upon contact with the zeolite or compositions, with the scent or odor being completely eliminated within about 1 to about 3 minutes. The zeolite or composition is applied at concentrate of about 1 to about 2 oz. per application. Additional amounts or dosage applications of the zeolite or compositions can be applied depending on strength of scent or odor.

The present disclosure is further defined by the following numbered paragraphs:

A composition comprising: zeolite, monocalcium phosphate, and desiccant, wherein the composition is a dry flowable powder.

The composition of paragraph 1, wherein the zeolite is a natural zeolite comprising a network of oxygen, silicon, and aluminum.

The composition of paragraph 2, wherein the natural zeolite is from a sedimentary origin.

The composition of any one of paragraphs 1-3, wherein the monocalcium phosphate is made by a process of combining phosphoric acid, water, and brown mud.

The composition of any one of paragraphs 1-4, wherein the desiccant is an activated alumina desiccant.

The composition of paragraph 5, wherein the desiccant is an aluminosilicate.

The composition of any one of paragraphs 1-6, wherein the powders are less than about 100 mesh (149 um or 0.0059 inches).

The composition of any one of paragraphs 1-7, wherein the composition has a free moisture content less than about 12%.

The composition of any one of paragraphs 1-8, wherein the zeolite comprises from about 60 wt-% to about 99 wt-% of the composition, the desiccant comprises from about 0.01 wt-% to about 20 wt-% of the composition, and the monocalcium phosphate comprises from about 0.01 wt-% to about 20 wt-% of the composition.

The composition of any one of paragraphs 1-8, wherein the zeolite comprises from about 80 wt-% to about 99 wt-% of the composition, the desiccant comprises from about 0.01 wt-% to about 10 wt-% of the composition, and the monocalcium phosphate comprises from about 0.01 wt-% to about 10 wt-% of the composition.

The composition of any one of paragraphs 1-10, wherein the composition comprises at least one additional functional ingredient.

The composition of any one of paragraphs 1-11, wherein the composition is free of liquid components, odor masking components and/or fragrances.

A method of employing the composition of any one of paragraphs 1-12 within its applicable or intended environment.

A system for eliminating odor and scent comprising: zeolite or the composition according to any one of paragraphs 1-12, and a dosing apparatus.

The system of paragraph 14, wherein the dosing apparatus is a porous housing.

The system of paragraph 15, wherein the porous housing is a pouch, sock or other fabric container selected based on the particle size of the zeolite or the composition.

The system of paragraph 16, where the porous housing provides a controlled dispensing thereof of the zeolite or the composition from the porous housing.

The system of paragraph 16, where the porous housing contains the zeolite or the composition inside the porous housing and air containing odor and scents passes through the porous housing.

The system of paragraph 14, wherein the dosing apparatus is a non-porous housing and further comprises a dispensing element (e.g., perforated lid, sealed lid, squeezable top).

The system of any one of paragraphs 14-19, wherein the dosing apparatus contains from about 1 oz. to about 120 oz. of the zeolite or the composition.

The system of any one of paragraphs 14-19, further comprising an outer container, preferably a sealed outer container.

A method of employing the system of any one of paragraphs 14-21 within its applicable or intended environment.

A method of eliminating scent or odor comprising: contacting an object or surface with a zeolite or the composition according to any one of paragraphs 1-12, and eliminating scents and/or odors.

The method of paragraph 23, wherein the object or surface comprises a soft surface, hard surface, portion of a users' body or apparel, the air, etc.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

The compositions as described in Table 1 were applied and tested by hunters to be able to gain closer proximity to hunted animals. In one application a hunter reported applying the composition to a ground blind out that was set in place as cover for hunting. The composition was applied directly to the ground blind out and to the hunter's outer wear (i.e., gear). The hunter applied the composition again just as shooting hours began and was able to gain close proximity to a bear that walked directly up to the ground blind out to be within inches of the hunter, a proximity which would not be achieved without the elimination of all of the scents and odors of the hunter. The bear was not able to ascertain by smell the presence of the hunter, demonstrating efficacy of the compositions and the methods of use.

Example 2

Again, the compositions as described in Table 1 were applied and tested by hunters to be able to gain as close of proximity to hunted animals. The hunter applied the compositions to all outerwear to eliminate scent. The hunter reported a small doe walked past the blind at five yards and then walked directly into the scent cone, which is a space where an animal is clearly able to detect scent of a predator. The doe made movements to suggest there was a change in the scent but did not detect the scent to be human scent as the doe calmed her flight response. The hunter was able to also get into close proximity to later harvest a buck.

It is to be understood that while the invention has been described in conjunction with the detailed description thereof, the foregoing description is intended to illustrate, and not limit the scope of the invention, which is defined by the scope of the appended claims. Other embodiments, advantages, and modifications are within the scope of the following claims. Any reference to accompanying drawings which form a part hereof, are shown, by way of illustration only. It is understood that other embodiments may be utilized, and structural changes may be made without departing from the scope of the present disclosure. All publications discussed and/or referenced herein are incorporated herein in their entirety.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

What is claimed is:

1. A composition consisting of:
zeolite,
monocalcium phosphate, and
desiccant,
   wherein the composition is a dry flowable powder and less than about 100 mesh (149 um or 0.0059 inches) in size.

2. The composition of claim 1, wherein the zeolite is a natural zeolite comprising a network of oxygen, silicon, and aluminum.

3. The composition of claim 2, wherein the natural zeolite is from a sedimentary origin.

4. The composition of claim 1, wherein the monocalcium phosphate is made by a process of combining phosphoric acid, water, and mud.

5. The composition of claim 1, wherein the desiccant is an activated alumina desiccant or an aluminosilicate.

6. The composition of claim 1, wherein the zeolite comprises from about 60 wt-% to about 99 wt-% of the composition, the desiccant comprises from about 0.01 wt-% to about 20 wt-% of the composition, and the monocalcium phosphate comprises from about 0.01 wt-% to about 20 wt-% of the composition, or wherein the zeolite comprises from about 80 wt-% to about 99 wt-% of the composition, the desiccant comprises from about 0.01 wt-% to about 10 wt-% of the composition, and the monocalcium phosphate comprises from about 0.01 wt-% to about 10 wt-% of the composition.

7. The composition of claim 1, wherein the composition is free of liquid components, odor masking components and/or fragrances.

8. A system for eliminating odor and scent comprising:
zeolite or the composition according to claim 1, and
a dosing apparatus.

9. The system of claim 8, wherein the dosing apparatus is a porous housing.

10. The system of claim 9, wherein the porous housing is a pouch or other fabric container selected based on the particle size of the zeolite or the composition.

11. The system of claim 9, wherein the porous housing provides a controlled dispensing thereof of the zeolite or the composition from the porous housing.

12. The system of claim 9, wherein the porous housing contains the zeolite or the composition inside the porous housing and air containing odor and scents passes through the porous housing.

13. The system of claim 8, wherein the dosing apparatus is a non-porous housing and further comprises a dispensing element, and optionally wherein the dispensing element comprises a perforated lid, sealed lid, or squeezable top.

14. The system of claim 8, wherein the dosing apparatus contains from about 1 oz. to about 120 oz. of the zeolite or the composition.

15. The system of claim 8, further comprising an outer container, and optionally wherein the outer container is a sealed outer container.

16. A method of eliminating scent or odor comprising:
contacting an object or surface with a zeolite or the composition according to claim 1, and eliminating scents and/or odors.

17. The method of claim 16, wherein the object or surface comprises a soft surface, hard surface, portion of a users' body or apparel, and/or the air.

18. The method of claim 16, wherein the scents and/or odors are from a human.

* * * * *